US006448019B1

(12) United States Patent
Mendelsohn et al.

(10) Patent No.: US 6,448,019 B1
(45) Date of Patent: *Sep. 10, 2002

(54) METHODS FOR IDENTIFYING VASOPROTECTIVE AGENTS

(75) Inventors: Michael E. Mendelsohn, Wellesley; Richard H. Karas, Franklin, both of MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/410,820

(22) Filed: Oct. 1, 1999

Related U.S. Application Data

(60) Continuation of application No. 09/040,089, filed on Mar. 17, 1998, now abandoned, which is a division of application No. 08/684,704, filed on Jul. 19, 1996, now Pat. No. 5,728,534.

(51) Int. Cl.[7] .......................... G01N 33/53; C12Q 1/68; C12P 19/34; C12N 1/38

(52) U.S. Cl. ...................... 435/7.1; 435/7.72; 435/7.8; 435/6; 435/69.1; 435/91.1; 435/91.2; 435/325; 435/375; 435/244

(58) Field of Search ....................... 435/7.1, 7.8, 7.72, 435/244, 325, 375

(56) References Cited

U.S. PATENT DOCUMENTS

| 5,071,773 A | 12/1991 | Evans et al. |
| 5,512,483 A | 4/1996 | Mader et al. |
| 5,580,722 A | 12/1996 | Foulkes et al. |
| 5,597,693 A | 1/1997 | Evans et al. |

FOREIGN PATENT DOCUMENTS

| WO | WO 94/23068 | 10/1994 |
| WO | WO 95/11973 | 5/1995 |
| WO | WO 95/31722 | 11/1995 |

OTHER PUBLICATIONS

Farhat et al. FASE J. 1996, Apeil vol. 10, pp. 615–624. The vascular protective effects of estrogen.*
Gustafsson, "Estrogen Receptor β–Getting in on the Action?," *Nature Medicine* 3:493–494 (1997).
Iafrati et al., "Estrogen Inhibits the Vascular Injury Response in Estrogen Receptor α–Deficient Mice," *Nature Medicine* 3:545–548 (1997).
Karas, "Estrogen Plays Crucial role in Preventing CAD; Hormone Replacement Reduces Risk For Postmenopausal Women," *Progress Notes* p. 5 and 10 (1996).
Karas et al., "Human Vascular Smooth Muscle Cells Contain Functional Estrogen Receptor," *Circulation* 89:1943–1950 (1994).

Karas et al., "Crosstalk Between Growth Regulatory and Estrogen Signaling Pathways in Human Vascular Smooth Muscle Cells," Abstract *Circulation* 90:I129 (1994).
Karas et al., "Inhibition of Vascular Smooth Muscle Cell Growth by Estrogen," Abstract *Circulation* 88:I325 (1993).
Karas et al., "Estrogen–Independent Activation of the Estrogen Receptor in Human Vascular Smooth Muscle Cells," Abstract *Circulation* 94:I595 (1996).
Karas et al., "Growth Factor Activation of the Estrogen Receptor in Vascular Cells Occurs Via a Mitogen–Activated Protein Kinase–Independent Pathway," *Journal of Clinical Investigation* 101:2851–2861 (1998).
Koike et al., "Differential–Display Polymerase Chain Reaction Identifies Nucleophosmin as an Estrogen–Regulated Gene in Human Vascular Smooth Muscle Cells," *Journal of Vascular Surgery* 23:477–482 (1996).
Kuiper et al., "Cloning of a Novel Estrogen Receptor Expressed in Rat Prostate and Ovary," *Proceedings of the National Academy of Science USA* 93:5925–5930 (1996).
Mendelsohn et al., "Estrogen and the Blood Vessel Wall," *Current Opinion in Cardiology* 9:619–626 (1994).
Mosselman et al., "Erβ: Identification and Characterization of a Novel Human Estrogen Receptor," *FEBS Letters* 392:49–53 (1996).
Sullivan et al., "Estrogen Inhibits the Response–to–Injury in a Mouse Carotid Artery Model," *Journal of Clinical Investigation* 96:2482–2488 (1995).

* cited by examiner

*Primary Examiner*—Elizabeth Kemmerer
*Assistant Examiner*—Sarada C Prasad
(74) *Attorney, Agent, or Firm*—Clark & Elbing LLP

(57) ABSTRACT

The invention features screening methods which can be used to identify agents, known as vasoprotective agents, which inhibit vascular smooth muscle cell activation and/or proliferation or enhance vascular endothelial cell activation and/or proliferation or activate estrogen responsive genes in vascular cells. Preferred vasoprotective agents are relatively vasospecific, i.e., their effect on one or more types of vascular cells is more pronounced than their effect on other cell types. Treatment with such vasospecific agents will generally be associated with fewer undesirable side-effects than treatment with estrogen. The methods of the invention are screening assays in which candidate agents are examined to identify vasoprotective agents. One type of screening assay involves examining the effect of a candidate agent on cell proliferation and/or cell activation. Another type of screening assay involves examining the effect of a candidate agent on the expression of a gene which is responsive to estrogen. Both screening assays involve the use of vascular cells and non-vascular cells. The use of both cell types is important because the cellular milieu is very likely to influence the effect of a candidate agent on cell proliferation, cell activation, and the expression of an given estrogen receptor responsive gene.

12 Claims, No Drawings

METHODS FOR IDENTIFYING VASOPROTECTIVE AGENTS

This application is a continuation of U.S. application Ser. No. 09/040,089, filed Mar. 17, 1998, now abandoned, which is a divisional of U.S. application Ser. No. 08/684,704, filed Jul. 19, 1996, now U.S. Pat. No. 5,728,534.

BACKGROUND OF THE INVENTION

Vascular diseases are the major cause of morbidity and mortality in the United States. Despite decades of intensive research, the mechanisms responsible for these diseases are poorly understood.

The low incidence of vascular diseases in pre-menopausal women and the rapid increase in vascular diseases, including cerebrovascular and ischemic heart disease, in women following the menopause are well recognized. It is now recognized that the hormone estrogen plays a significant role in preventing atherosclerotic vascular disease. Most attempts to explain the effects of estrogen on the development of vascular disease in women focus on indirect effects of estrogen on known risk factors, such as lipid and/or carbohydrate metabolism, counterbalancing of androgen-mediated effects, or indirect effects of sex hormones on the thrombotic milieu.

Estrogen replacement therapy has been rather successful in reducing the incidence of vascular disease in post-menopausal women. It can reduce the incidence of coronary artery disease by as much as 30–50 percent. However, estrogen replacement therapy has a number of significant drawbacks, including an increased risk of endometrial cancer, an increased risk of breast cancer in women, and side effects such as endometrial bleeding and breast tenderness. In addition, though estrogen therapy may theoretically have beneficial effects for vascular disease in men as well as women, attempts to examine this possibility have been limited by adverse effects observed with currently available agents and the possibility of feminization that such therapy harbors.

There is a need for more selective therapies which have some or all of the vasoprotective benefits of estrogen therapy, but have fewer undesirable side-effects.

SUMMARY OF THE INVENTION

The present invention relates to screening methods which can be used to identify agents which inhibit vascular smooth muscle cell activation and/or proliferation or enhance vascular endothelial cell activation and/or proliferation or activate estrogen responsive genes in vascular cells. Such agents are potentially useful for treatment or prevention of vascular disease and are referred to as "vasoprotective agents." Preferred vasoprotective agents are relatively vasospecific, i.e., their effect on one or more types of vascular cells is more pronounced than their effect on other cell types. Treatment with such vasospecific agents will generally be associated with fewer undesirable side-effects than treatment with estrogen. Vascular disease can result from over-proliferation of vascular smooth muscle cells. This proliferation can be inhibited by activation and/or proliferation of vascular endothelial cells. For example, a preferred agent would inhibit the proliferation of vascular smooth muscle cells and/or increase proliferation of vascular endothelial cells associated with the development of atherosclerosis, but not have any significant effect on cells of the reproductive system, e.g., breast cells or uterine cells.

The methods of the invention permit identification of agents which inhibit vascular smooth muscle cell proliferation directly by altering the proliferation rate of vascular smooth muscle cells. The methods of the invention also permit identification of agents which inhibit vascular smooth muscle cell proliferation more indirectly by enhancing the proliferation or activation of vascular endothelial cells, which can, in vivo, exert an inhibitory effect on the proliferation of vascular smooth muscle cells and can also promote vascular stability through an increased rate or extent of re-endothelialization.

The term "vasoprotective agent" refers to agents which have the potential to reduce vascular disease in patients because they inhibit, directly or indirectly, unwanted proliferation of vascular smooth muscle cells and/or enhance, directly or indirectly, endothelial cell growth or regrowth at sites of vascular injury.

The methods of the invention are screening assays in which candidate agents are examined to identify vasoprotective agents. One type of screening assay involves examining the effect of a candidate agent on cell proliferation and/or cell activation. Another type of screening assay involves examining the effect of a candidate agent on the expression of a gene which is responsive to estrogen ("an estrogen responsive gene"). Both screening assays involve the use of vascular cells and non-vascular cells. The use of both cell types is important because the cellular milieu is very likely to influence the effect of a candidate agent on cell proliferation, cell activation, and the expression of an given estrogen receptor responsive gene.

The term "estrogen responsive gene" refers to a gene whose expression can be affected by the presence of an estrogen.

The methods of the invention can be used to identify agents which exert their effect through a known estrogen receptor, e.g., estrogen receptor α or estrogen receptor β, or through an as yet unidentified estrogen receptor ("estrogen receptor-dependent agent"). Moreover, the methods of the invention can be used to identify agents which exert their effect through a receptor other than an estrogen receptor. These other receptors may recognize the same DNA binding site (recognition element) as an estrogen receptor or may bind to a recognition element which is distinct from an estrogen receptor recognition element.

The term "estrogen receptor" means a protein which specifically binds an estrogen (e.g., 17β-estradiol or E2). Estrogen binding can be measured using any standard estrogen binding assay, e.g., the assay described by Gibson et al. (*Endocrinology*, 29:2000, 1991). The term encompasses, but is not limited to, both the well-known estrogen receptor α (Green et al., *Nature* 320:134,1986) and the more recently described estrogen receptor β (Kuiper et al., *Proc. Nat'l Acad. Sci. USA* 93:5925, 1996; Genbank Accession Number U57439).

The term "estrogen receptor-dependent agent" refers to an agent the effect of which on a cell depends on the presence of an estrogen receptor (e.g., estrogen receptor α or estrogen receptor β or some other estrogen receptor) in the cell. Accordingly, the term includes agents which have one effect on a cell when an estrogen receptor is expressed by the cell and a different effect or no effect on the same cell when an estrogen receptor is not expressed by the cell. The agent may, of course, exert other effects which are not mediated via the estrogen receptor. Tamoxifen, 17β-estradiol, and ICI 182,780 are all examples of estrogen receptor-dependent agents.

In selecting a vasoprotective agent, among the undesirable side-effects to be avoided or minimized are activating or growth promoting effects on: (a) cancerous cells or pre-cancerous cells; (b) uterine cells or tissue; (c) breast cells or tissue; and (d) non-vascular, non-reproductive cells. Of course, it may not be possible to completely avoid all or even some of these undesirable side-effects in selecting a vasoprotective agent. A vasoprotective agent can be therapeutically beneficial even if its use is associated to some extent with some or all of these side effects.

In addition to identifying vasoprotective agents which avoid or minimize undesirable side effects, it is desirable to identify vasoprotective agents which are osteoprotective. The term "osteoprotective agent" refers to agents which have the potential to reduce osteoporosis in patients because they increase the activation and/or proliferation of osteoclasts, which are responsible for bone formation, or because they inhibit activation and/or proliferation of osteoclasts, which are responsible for bone absorbtion.

Some of the methods which can be used to identify vasoprotective agents involve measuring cell activation and/or proliferation. Cell proliferation can be measured by measuring cell number, DNA content, or $^3$H-thymidine uptake. Cell activation can be monitored by measuring the expression of genes that are up regulated by cell activation. For example, to monitor activation of vascular smooth muscle cells, expression of inducible nitric oxide synthase or vascular endothelial cell growth factor can be measured. To monitor the activation of vascular endothelial cells, expression of prostacyclin synthase or endothelial nitric oxide synthase can be measured.

Other methods which can be used to identify vasoprotective agents involve measuring the expression of an estrogen responsive gene. The effect of a candidate agent on the expression of an estrogen receptor responsive gene can often be most easily measured through the use of a reporter construct in which the upstream regulatory region of an estrogen responsive gene (or an estrogen responsive element) is operably linked to a readily measurable protein, e.g., luciferase. Among the estrogen responsive genes whose upstream regulatory regions can be employed in the methods of the invention are the vitellogenin gene, the progesterone receptor gene, the prolactin receptor gene, the nuceleophosmin gene, and the vascular endothelial cell growth factor gene.

The invention feature a method for evaluating whether an agent is a vasoprotective agent, which method includes:
  (a) culturing vascular endothelial cells containing a non-endogenous reporter construct in the presence of the agent, the non-endogenous reporter construct comprising an estrogen responsive element operatively linked to a reporter gene;
  (b) culturing non-vascular cells containing the non-endogenous reporter construct in the presence of the agent; and
  (c) measuring the expression of the reporter gene in the vascular endothelial cells in the presence of the agent and measuring the expression of the reporter gene in the non-vascular cells in the presence of the agent;
  whereby, an agent is identified as a vasoprotective agent when the expression of the reporter gene in the vascular endothelial cells in the presence of the agent compared to the expression of the reporter in control vascular endothelial cells is greater than the expression of the reporter gene in the non-vascular cells in the presence of the agent compared to the expression of the reporter gene in control non-vascular cells.

The invention features a method for evaluating whether an agent is a vasoprotective agent, which method includes:
  (a) culturing vascular smooth muscle cells containing a non-endogenous reporter construct in the presence of the agent, the non-endogenous reporter construct comprising an estrogen responsive element operatively linked to a reporter gene;
  (b) culturing non-vascular cells containing the non-endogenous reporter construct in the presence of the agent; and
  (c) measuring the expression of the reporter gene in the vascular smooth muscle cells in the presence of the agent and measuring the expression of the reporter gene in the non-vascular cells in the presence of the agent;
  whereby, an agent is identified as a vasoprotective agent when the expression of the reporter gene in the vascular smooth muscle cells in the presence of the agent compared to the expression of the reporter in control vascular smooth muscle cells is less than the expression of the reporter gene in the non-vascular cells in the presence of the agent compared to the expression of the reporter gene in control non-vascular cells.

The invention features a method for evaluating whether an agent is a vasoprotective agent, which method includes:
  (a) culturing vascular endothelial cells containing a non-endogenous reporter construct in the presence of the agent, the non-endogenous reporter construct comprising an estrogen responsive element operatively linked to a reporter gene;
  (b) culturing null cells containing the non-endogenous reporter construct in the presence of the agent, the null cells being cells which do not express an estrogen receptor; and
  (c) measuring the expression of the reporter gene in the vascular endothelial cells in the presence of the agent and measuring the expression of the reporter gene in the null cells in the presence of the agent;
  whereby, an agent is identified as a vasoprotective agent when the expression of the reporter gene in the vascular endothelial cells in the presence of the agent compared to the expression of the reporter in control vascular endothelial cells is greater than the expression of the reporter gene in the null cells in the presence of the agent compared to the expression of the reporter gene in control null cells.

The invention features a method for evaluating whether an agent is a vasoprotective agent, which method includes:
  (a) culturing vascular smooth muscle cells containing a non-endogenous reporter construct in the presence of the agent, the non-endogenous reporter construct comprising an estrogen is responsive element operatively linked to a reporter gene;
  (b) culturing null cells containing the non-endogenous reporter construct in the presence of the agent, the null cells being cells which do not express an estrogen receptor; and
  (c) measuring the expression of the reporter gene in the vascular smooth muscle cells in the presence of the agent and measuring the expression of the reporter gene in the null cells in the presence of the agent;
  whereby, an agent is identified as a vasoprotective agent when the expression of the reporter gene in the vascular smooth muscle cells in the presence of the agent compared to the expression of the reporter in control vascular smooth muscle cells is less than the expression of the reporter gene in the null cells in the presence of the agent compared to the expression of the reporter gene in control null cells.

The invention features a method for evaluating whether an agent is a vasoprotective agent, which method includes:
(a) culturing vascular endothelial cells containing a non-endogenous reporter construct in the presence of the agent, the non-endogenous reporter construct comprising an estrogen responsive element operatively linked to a reporter gene;
(b) culturing vascular smooth muscle cells containing the non-endogenous reporter construct in the presence of the agent; and
(c) measuring the expression of the reporter gene in the vascular endothelial cell in the presence of the agent and measuring the expression of the reporter gene in the vascular smooth muscle cells in the presence of the agent;
whereby, an agent is identified as a vasoprotective agent when the expression of the reporter gene in the vascular endothelial cells in the presence of the agent compared to the expression of the reporter in control vascular endothelial cells is greater than the expression of the reporter gene in the vascular smooth muscle cells in the presence of the agent compared to the expression of the reporter gene in control smooth muscle cells.

The invention features a method for evaluating whether an agent is a vasoprotective agent, which method includes:
(a) culturing vascular smooth muscle cells in the presence of the agent;
(b) culturing null cells in the presence of the agent, the null cells being cells which do not express an estrogen receptor; and
(c) measuring the rate of proliferation of the vascular smooth muscle cells in the presence of the agent and measuring the rate of proliferation of the null cells in the presence of the agent;
whereby, an agent is identified as a vasoprotective agent when the rate of proliferation of the vascular smooth muscle cells in the presence of the agent compared to the rate of proliferation of control vascular smooth muscle cells is less than the rate of proliferation of the null cells in the presence of the agent compared to control null cells.

The invention features a method for evaluating whether an agent is a vasoprotective agent, which method includes:
(a) culturing vascular endothelial cells in the presence of the agent;
(b) culturing null cells in the presence of the agent, the null cells being cells which do not express an estrogen receptor; and
(c) measuring the rate of proliferation of the vascular endothelial cells in the presence of the agent and measuring the rate of proliferation of the null cells in the presence of the agent;
whereby, an agent is identified as a vasoprotective agent when the rate of proliferation of the vascular endothelial cells in the presence of the agent compared to the rate of proliferation of control vascular endothelial cells is greater than the rate of proliferation of the null cells in the presence of the agent compared to control null cells.

The invention features a method for evaluating whether an agent is a vasoprotective agent, which method includes:
(a) culturing vascular endothelial cells in the presence of the agent;
(b) culturing vascular smooth muscle cells in the presence of the agent, the null cells being cells which do not express an estrogen receptor; and
(c) measuring the rate of proliferation of the vascular endothelial cells in the presence of the agent and measuring the rate of proliferation of the vascular smooth muscle cells in the presence of the agent;
whereby, an agent is identified as a vasoprotective agent when the rate of proliferation of the vascular endothelial cells in the presence of the agent compared to the rate of proliferation of control vascular endothelial cells is greater than the rate of proliferation of the vascular smooth muscle cells in the presence of the agent compared to control vascular smooth muscle cells.

The invention features a method for evaluating whether an agent is a vasoprotective agent, which method includes:
(a) culturing vascular endothelial cells containing a non-endogenous reporter construct in the presence of the agent, the non-endogenous reporter construct comprising functional regulatory sequences derived from a growth promoting gene operatively linked to a reporter gene;
(b) culturing non-vascular cells containing the non-endogenous reporter construct in the presence of the agent; and
(c) measuring the expression of the reporter gene in the vascular endothelial cells in the presence of the agent and measuring the expression of the reporter gene in the non-vascular cells in the presence of the agent;
whereby, an agent is identified as a vasoprotective agent when the expression of the reporter gene in the vascular endothelial cells in the presence of the agent compared to the expression of the reporter in control vascular endothelial cells is greater than the expression of the reporter gene in the vascular smooth muscle cells in the presence of the agent compared to the expression of the reporter gene in control smooth muscle cells.

The invention features a method for evaluating whether an agent is a vasoprotective agent, which method includes:
(a) culturing vascular smooth muscle cells containing a non-endogenous reporter construct in the presence of the agent, the non-endogenous reporter construct comprising functional regulatory sequences derived from a growth promoting gene operatively linked to a reporter gene;
(b) culturing null cells containing the non-endogenous reporter construct in the presence of the agent, the null cells being cells which do not express an estrogen receptor; and
(c) measuring the expression of the reporter gene in the vascular smooth muscle cells in the presence of the agent and measuring the expression of the reporter gene in the non-vascular cells in the presence of the agent;
whereby, an agent is identified as a vasoprotective agent when the expression of the reporter gene in the vascular smooth muscle cells in the presence of the agent compared to the expression of the reporter in control vascular smooth muscle cells is less than the expression of the reporter gene in the non-vascular cells in the presence of the agent compared to the expression of the reporter gene in control non-vascular cells.

The invention features a method for evaluating whether an agent is a vasoprotective agent, which method includes:
(a) culturing vascular endothelial cells containing a non-endogenous reporter construct in the presence and absence of the agent, the non-endogenous reporter construct comprising functional regulatory sequences derived from a growth promoting gene operatively linked to a reporter gene;

(b) culturing vascular smooth muscle cells containing the non-endogenous reporter construct in the presence and absence of the agent; and (c) measuring the expression of the reporter gene in the vascular endothelial cells in the presence of the agent and measuring the expression of the reporter gene in the vascular smooth muscle cells in the presence of the agent;

whereby, an agent is identified as a vasoprotective agent when the expression of the reporter gene in the vascular endothelial cells in the presence of the agent compared to the expression of the reporter in control vascular endothelial cells is greater than the expression of the reporter gene in the vascular smooth muscle cells in the presence of the agent compared to the expression of the reporter gene in control vascular smooth muscle cells.

The invention features a method for evaluating whether an agent is a vasoprotective agent, which method includes:

(a) culturing vascular endothelial cells containing a non-endogenous reporter construct in the presence of the agent, the non-endogenous reporter construct comprising functional regulatory sequences derived from a growth arrest gene operatively linked to a reporter gene;

(b) culturing non-vascular cells containing the non-endogenous reporter construct in the presence of the agent; and (c) measuring the expression of the reporter gene in the vascular endothelial cells in the presence of the agent and measuring the expression of the reporter gene in the non-vascular cells in the presence of the agent;

whereby, an agent is identified as a vasoprotective agent when the expression of the reporter gene in the vascular endothelial cells in the presence of the agent compared to the expression of the reporter in control vascular endothelial cells is less than the expression of the reporter gene in the vascular smooth muscle cells in the presence of the agent compared to the expression of the reporter gene in control smooth muscle cells.

The invention features a method for evaluating whether an agent is a vasoprotective agent, which method includes:

(a) culturing vascular smooth muscle cells containing a non-endogenous reporter construct in the presence of the agent, the non-endogenous reporter construct comprising functional regulatory sequences derived from a growth arrest gene operatively linked to a reporter gene;

(b) culturing null cells containing the non-endogenous reporter construct in the presence of the agent, the null cells being cells which do not express an estrogen receptor; and (c) measuring the expression of the reporter gene in the vascular smooth muscle cells in the presence of the agent and measuring the expression of the reporter gene in the non-vascular cells in the presence of the agent;

whereby, an agent is identified as a vasoprotective agent when the expression of the reporter gene in the vascular smooth muscle cells in the presence of the agent compared to the expression of the reporter in control vascular smooth muscle cells is greater than the expression of the reporter gene in the non-vascular cells in the presence of the agent compared to the expression of the reporter gene in control non-vascular cells.

The invention features a method for evaluating whether an agent is a vasoprotective agent, which method includes:

(a) culturing vascular endothelial cells containing a non-endogenous reporter construct in the presence and absence of the agent, the non-endogenous reporter construct comprising functional regulatory sequences derived from a growth arrest gene operatively linked to a reporter gene;

(b) culturing vascular smooth muscle cells containing the non-endogenous reporter construct in the presence and absence of the agent; and (c) measuring the expression of the reporter gene in the vascular endothelial cells in the presence of the agent and measuring the expression of the reporter gene in the vascular smooth muscle cells in the presence of the agent;

whereby, an agent is identified as a vasoprotective agent when the expression of the reporter gene in the vascular endothelial cells in the presence of the agent compared to the expression of the reporter in control vascular endothelial cells is less than the expression of the reporter gene in the vascular smooth muscle cells in the presence of the agent compared to the expression of the reporter gene in control vascular smooth muscle cells.

In each of the assays described herein the expression of a reporter gene in a cell grown in the presence of an agent is always corrected by comparison to the expression of a reporter gene in an otherwise identical cell grown in the absence of the agent.

The term "estrogen responsive element" refers to a DNA sequence element which confers upon a gene to which it is operably linked responsiveness to the presence of an estrogen. The so-called consensus estrogen receptor α response element, is an example of an estrogen responsive element. Estrogen responsive elements can be found in the upstream regulatory region of estrogen reponsive genes, e.g., the human VEGF gene or the vitellogenin gene. While the entire upstream regulatory region of an estrogen responsive gene can be used as an estrogen responsive element, it is also possible to identify one or more smaller estrogen responsive elements within the upstream regulatory region. This is because an estrogen responsive element includes the smallest unit which confers estrogen responsiveness.

A "reporter gene" is a sequence which includes a mammalian promoter, a sequence encoding a detectable protein, e.g., luciferase, and, in most cases, a poly(A) signal sequence. Reporter genes are routinely used to investigate upstream regulatory regions. Generally, all or a portion of an upstream regulatory region of interest is position upstream (5') of the reporter gene promoter and the entire construct is introduced into a selected cell type to study the effect of the selected upstream region on expression of the protein encoded by the reporter gene. Reporter genes are often inserted into vectors. For example, the pGL3-Promoter Vector (Promega, Madison, Wis.) is a vector which contains an SV40 promoter upsteam of a firefly luciferase gene (including a polyA signal sequence). The vector includes sequences required for replication of the vector in *E. coli* and mammalian cells.

A sequence element is "operably linked" to a reporter gene when it is inserted upstream of the reporter gene promoter such that can influence expression of the protein encoded by the gene. For example, an estrogen responsive element inserted into the polylinker found upstream of the SV40 promoter in pGL3-Promoter Vector is operably linked to the luciferase reporter gene.

In various preferred embodiments the vascular, non-vascular, or null cells are stably transfected with the non-endogenous reporter construct; the vascular, non-vascular, or null cells are co-transfected with an estrogen receptor expression construct. In more preferred embodiments the estrogen receptor expression construct expresses estrogen receptor α and the estrogen receptor expression construct expresses estrogen receptor β.

In another aspect the invention features a vascular endothelial cell containing an estrogen receptor β expression construct. In yet another aspect the invention features a vascular smooth muscle cell containing an estrogen receptor β expression construct.

In another aspect the invention features cells of cell line WB572. In preferred embodiments the WB572 cells contain a non-endogenous reporter construct comprising an estrogen responsive element operatively linked to a reporter gene, contain an estrogen receptor α expression construct, and contain an estrogen receptor β expression construct. In more preferred embodiments the estrogen receptor α expression construct is an inducible expression construct and the estrogen receptor β expression construct is an inducible expression construct.

In all assays entailing the measurement and comparison of cell proliferation rates the measured rate of proliferation of a given cell type in the presence of an agent is always corrected for the rate of proliferation of a control cell. The control cell is an otherwise identical cell grown in the absence of the agent being tested.

When measuring and comparing proliferation rates it should be understood that some vasoprotective agents may actually reduce the rate of proliferation of certain cell types. For example, a desirable vasoprotective agent might not substantially change the rate of proliferation of a selected strain of vascular endothelial cell while decreasing the rate of proliferation of a selected strain of vascular smooth muscle cells.

In various preferred embodiments the vascular, non-vascular, or null cells are stably transfected with the non-endogenous reporter construct; the vascular, non-vascular, or null cells are co-transfected with an estrogen receptor expression construct. In more preferred embodiments the estrogen receptor expression construct expresses estrogen receptor α and the estrogen receptor expression construct expresses estrogen receptor β.

DETAILED DESCRIPTION

Described below are various methods for screening candidate agents to identify vasoprotective agents.

The methods of the invention rely on examining the effect of various agents based on either its effect on the growth and/or activation of particular cell types (e.g., vascular and non-vascular) or its effect on the expression of an estrogen responsive gene in particular cell types. The cellular context is critical because the expression of a gene under the control of an estrogen receptor may also be affected by one or more additional factors, such as co-activators (e.g., SRC-1), repressors (e.g., NCOR/SMRT), or other expression modulating proteins which may be cell specific. Cell specific factors include those factors which may or may not be expressed in a given cell type or which may be expressed at different levels in different cell types. Although these additional factors can contribute to the cell-type specific nature of gene activation by a steroid hormone receptor such as the estrogen receptor, the methods of the invention do not require an understanding of these additional factors.

A vasoprotective agent can be identified based on either its effect on the growth and/or activation of particular cell types (e.g., vascular and non-vascular) or its effect on the expression of an estrogen responsive gene in particular cell types (e.g., vascular and non-vascular).

The effect of a given agent on cell growth and/or activation can be measured either directly or indirectly. Direct measurement of cell growth and/or activation involves monitoring cell proliferation or activation. Indirect measurement of cell growth and/or activation involves monitoring the expression of genes encoding cell growth promoting factors and/or monitoring the expression of genes encoding cell growth arrest factors. In general, the expression of these genes is monitored indirectly by monitoring the expression of a reporter construct in which all or part of the upstream regulatory region of the gene of interest is operably linked to a sequence encoding a readily detectable protein.

As noted above, a vasoprotective agent can also be identified based on its effect on the expression of an estrogen responsive gene in particular cell types. An estrogen responsive gene can be a naturally-occurring gene which is responsive to estrogen, e.g., the vascular endothelial cell growth factor gene. The effect of an agent on the expression of such a naturally-occurring estrogen-responsive gene can be measured directly or indirectly. Direct measurement involves monitoring the expression of the estrogen responsive gene itself. One can measure the expression of a genomic copy of the gene or one can measure the expression of a non-endogenous copy of the gene, e.g., a copy introduced by transfection. Generally, expression of the estrogen responsive gene is monitored by measuring MRNA production. Alternatively, protein production can be measured. In many cases it is preferable to indirectly monitor the expression of an estrogen responsive gene by monitoring the expression of a reporter construct in which all or part of the upstream regulatory region of the estrogen responsive gene of interest is operably linked to a sequence encoding a readily detectable protein. Another type of estrogen responsive gene is a wholly synthetic gene in which sequences known to confer estrogen responsiveness are operably linked to a sequence encoding a readily detectable protein. A luciferase encoding reporter construct in which luciferase expression is under the control of a consensus estrogen receptor α recognition element is an example of such an estrogen responsive gene. Cells As discussed above, the methods of the invention identify an agent as a candidate vasoprotective agents by examining the effect of the agent on cell growth and/or activation or gene expression in two different cellular contexts: vascular and non-vascular. Accordingly, the methods of the invention can employ a variety of cell types.

Vascular cell lines of particular interest are: WB572 cells (spontaneously transformed human saphenous vein smooth muscle cells) and SV-E6 cells (human saphenous vein cells stably transfected with the E6 viral oncogene).

Other vascular cell lines useful in the method of the invention include, but are not limited to: A7R5 cells (spontaneously transformed rat thoratic aorta smooth muscle cells; ATCC, Bethesda, Md.; ECV304 cells (human umbilical vein vascular endothelial cells; ATCC, Bethesda, Md.); GH3B6 cells (rat pituitary cells; ATCC, Bethesda, Md.); PVEC cells (rat pulmonary vein endothelial cells; *J. Tissue Culture Res.* 10:9, 1986); CPA47 (bovine endothelial cells; ATCC CRL 1733); CPAE cells (bovine endothelial cells; ATCC CCL 209); EJG cells (bovine endothelial cells; ATCC CRL 8659); FBHE (bovine endothelial cells; ATCC CRL 1395); HW-EC-C cells (human endothelial cells; ATCC CRL 1730); and T/G HA-VSMC cells (human vascular smooth muscle cells; ATCC CRL 1999).

Non-vascular cell lines useful in the methods of the invention include, but are not limited to: MCF-7 cells (human breast cancer cells; ATCC, Bethesda, Md.); ZR-75-1 cells (human breast cancer; ATCC CRL-1500); UACC-893 cells (human breast cancer; ATCC CRL-1902); RL95-2 cells (human endometrial cancer; ATCC CRL-1671); KLE cells (human endometrial cancer; ATCC CRL-1622).

Cell lines which do not express estrogen receptor α, e.g., COS-1 cells, Cos-7 cells, CHO cells, HEK 293 cells, and HeLa cells, are useful in some embodiments of the invention.

Bone cell lines, e.g., UMR-106 cells (rat osteogenic sarcoma; ATCC CRL-1661) and HOS (human osteosarcoma; ATCC CRL-1543), are useful for determining whether a candidate vasoprotective agent is also osteoprotective.

Reporter Constructs

Reporter constructs are used to indirectly monitor the effect of an agent on the proliferation and/or activation of vascular cells and to monitor the effect of an agent on the expression of an estrogen responsive gene.

Reporters Based on Estrogen Responsive Genes

A number of reporter constructs in which all or a portion of the upstream regulatory region of an estrogen receptor responsive gene or an isolated estrogen receptor recognition element (ERE) is operably linked to a sequence encoding a detectable protein are useful in the methods of the invention.

In general, any gene which is responsive to an estrogen receptor can serve as the basis for a reporter construct. For example, the following vascular genes are potentially of interest: prostaglandin cyclooxygenase, prostaglandin synthase, nitric oxide synthase (constitutive or calcium-dependent), collagen, elastin, c-fos, progesterone receptor, vascular endothelial growth factor, epidermal growth factor receptor, interleukin-6, neu, egr-1, estrogen receptor, heat shock protein 27, vascular adhesion molecules, vascular smooth muscle cell calcium channels, ryanodine receptor, FLT4 receptor tyrosine kinase, fibroblast growth factor receptor, and inducible nitric oxide synthase. Other potentially estrogen responsive genes are described in Mendelsohn and Karas (*Current opinion in Cardiology* 9:619, 1994).

In some cases an estrogen responsive gene will also be a growth related gene. In these cases it the change is expression indicative of a vasoprotective agent may depend on the cell type. Thus, in the following list a "+" indicates that preferred agents increase expression of that gene (or a reporter operably linked to the upstream control region of that gene in the indicated cell type; a "−" indicates that preferred agents decrease expression of that gene (or a reporter operably linked to the upstream control region of that gene in the indicated cell type. In each case the format is (preferred response in vascular endothelial cells/preferred response in vascular smooth muscle cells): prostaglandin cyclooxygenase (+/+), prostaglandin synthase (+/+), nitric oxide synthase (constitutive or calcium-dependent) (+/+) collagen (−/−), elastin (−/−), c-fos (+/−), progesterone receptor (+/+), vascular endothelial growth factor (+/+), epidermal growth factor receptor (−/−), interleukin-6 (+/+), neu (−/−), egr-1 (−/−), estrogen receptor (+/+), heat shock protein 27 (+/−), vascular adhesion molecules (−/−), vascular smooth muscle cell calcium channels (−/−), ryanodine receptor (−/−), FLT4 receptor tyrosine kinase (+/−), fibroblast growth factor receptor (−/−), and inducible nitric oxide synthase (+/+).

All or part of the upstream regulatory region of a naturally-occurring estrogen responsive gene can be operably linked to the sequence encoding a detectable protein in order to provide a suitable reporter construct. The portion of the upstream regulatory region used must include a sequence which confers some degree of responsiveness to estrogen.

One useful reporter construct is pmVEGF-Luc. In this reporter construct, a 1.6 kB fragment of genomic DNA located upstream of the murine vascular endothelial cell growth factor (VEGF) gene has been inserted into the pGL2-Basic luciferase reporter plasmid (Promega; Madison, Wis.). The 1.6 kB fragment includes the transcription start site, 1.2 kB of sequence upstream of the start site, and 0.4 kB of sequence downstream of the start site. Useful variants of this reporter plasmid can be made by deleting a portion of the murine VEGF control region. For example, pVEGF-Luc-Apa/Kpn is identical to pVEGF-luc except that 455 bp at the 5' end of the 1.6 kB fragment have been removed; pVEGF-Luc-Mlu is identical to pVEGF-luc except that 768 bp at the 5' end of the 1.6 kB fragment have been removed; and pVEGF-Luc-Sma is identical to pVEGF-luc except that 455 bp at the 5' end of the 1.6 kB fragment have been removed. Similar reporter constructs can be created using upstream regulatory sequences from the human VEGF gene. For example, phVEGF-Luc is a reporter construct in which 5.1 kb genomic DNA upstream of the human VEGF coding sequence inserted into the pGL2-Basic luciferase reporter plasmid. This particular construct includes 3.4 kb of sequence upstream of the VEGF transcription start site and 1.7 kb untranslated sequence downstream of the transcription start site.

Assays Based on Estrogen Resoonsive Reporters

Agents which activate the expression of estrogen responsive genes in vascular cells, but not in non-vascular cells are candidate vasoprotective agents. Generally, reporter constructs can be used to examine the effect of a given agent on the expression of such genes. Suitable reporter constructs can be created by placing a sequence encoding a readily detectable protein, e.g., luciferase, under the control of all or part the upstream transcription control region of an estrogen responsive gene. The portion of the upstream control region used in the reporter construct must include the recognition element(s) required for response to estrogen. Such elements can be identified based on their similarity to known estrogen receptor recognition elements or by functional dissection of the upstream regulatory region.

Alternatively, a reporter gene can be placed under the control of one or more synthetic estrogen receptor response elements. Such synthetic elements can be designed based on the sequence of known estrogen receptor response elements. Both types of constructs are referred to as estrogen responsive reporters.

To set up the assay, a selected estrogen responsive reporter is introduced into a vascular cell line (a vascular endothelial cell line or a vascular smooth muscle cell line) and a non-vascular cell line. The non-vascular cell line is preferably a cell line derived from a reproductive tissue (e.g, a breast cell line or a uterine cell line). The selected estrogen responsive reporter may also be introduced into a cell line which does not express estrogen receptor α or β (null cells). Suitable null cell lines include COS cells, HeLa cells, and HEK 293 cells. While the reporter can be introduced into the cells various cell lines by transient transfection, it is preferable that the cells be stably transfected with the reporter construct. Generally, human, urine, and/or rat cells can be used in the methods of the invention. In addition, the reporter constructs can employ the upstream regulatory sequences of human, murine, or rat estrogen responsive genes. Moreover, the cell line and the gene used as the source of upstream regulatory regions for the reporter construct do not have to be of the same species. Thus, a reporter in which the upstream control region of murine VEGF gene is operably linked to sequence encoding luciferase can be used in the screening methods of the invention.

There are three preferred formats for a screening assay which is based on an estrogen responsive reporter. All three formats involve at least two different cell types which harbor the same estrogen responsive reporter. The preferred assays use either vascular cells and non-vascular cells or vascular cells and null cells or two different types of vascular cells. However, other combinations may be used. Moreover, the vascular/non-vascular format and the vascular/vascular format can employ more than one vascular cell type (e.g., a vascular smooth muscle cell line and a vascular endothelial cell line or two different vascular endothelial cell lines) and more than one non-vascular cell type (e.g., a breast cell line and a uterine cell line). The use of two or more different cell lines of the same type in a single assay format is desirable because one can identify candidate vasoprotective agents which have the same or similar effect on several cells of the same type. The vascular null format can also employ more than one cell line of each type. In both formats one can use two or more different estrogen responsive reporter constructs.

EXAMPLE

Vascular Cell/Non-vascular Cell Format

The following example is meant to be illustrative, not limiting. For illustrative purposes, this example employs cells which save been stably transfected with a luciferase reporter construct. The assay, as described, is configured for cells grown in 96 well plates. The assay is not in any way confined to these characteristics and can equally well employ transiently transfected cells, reporter proteins other than luciferase, or cells grown in tissue culture wells of other sizes. These parameters were chosen as examples because they afford the considerable opportunity for automation and high throughput.

Cells are plated in 96 well plates in complete medium at 70% confluence. Each assay, which can accommodate 8 different cell lines, includes cells of vascular and non-vascular origin. After plating, the cells are allowed to rest undisturbed for 6 hours to allow attachment, and then each well is rinsed twice with 200 µl of serum free media and then re-fed with 200 µl of serum-free media that contains a candidate agent of interest. Each cell type is exposed to three different concentrations of the compound of interest and to control solution without the candidate agent. Each treatment is performed in triplicate. Thus, as configured here, each assay includes triplicate measurements of 8 cell lines under four different experimental conditions for a total of 96 samples. After 48 hours of incubation, the cells are lysed in situ in 50 µl of a solution compatible with the luciferase assay (Karas et al., *Circulation* 89:1943, 1994) and luciferase activity is determined spectrophotometrically (either manually by removal of the cell lysate from the tissue culture plate, or automatically in a computerized plate reader). Agents that increase the luciferase activity over control conditions in the vascular cells are identified as vasoactive agents. Agents that are vasoactive, but do not alter luciferase activity in the non-vascular are identified as candidate vasoprotective agents.

The general assay described above is amenable to variation in a number of ways. As noted above, the assay can be employ transiently transfected cells or stably transfected cells. The use of transiently transfected cells is particularly well suited to rapid testing of new cell lines to determine their suitability for further study. In some cell types, the level of activation of the estrogen responsive reporter construct may be low, and this may be augmented by co-transfection (again in either a transient or a stable fashion) of an estrogen receptor (or an isoform or mutant thereof) expression construct. In addition, the level of expression of the estrogen receptor expression construct can be controlled by use of a regulatable promotor such as the tetracycline-responsive system described below. Other means of regulating the estrogen receptor expression construct are also compatible with this screening assay.

EXAMPLE

Vascular Cell/Null Cell Format

The following example is for illustrative purposes only. A vascular smooth muscle cell line, WB572 cells, and a null cell line, COS cells, are stably transfected with the estrogen responsive reporter pERE-Luc. The cells are grown and treated as described above. Any increase in luciferase expression of treated WB572 cells compared to control cells is compared to the increase in luciferase expression of treated COS cells compared to control cells. An agent which increases luciferase expression in WB572 cells to a greater extent than COS cells is a candidate vasoprotective agent.

EXAMPLE

Vascular Cell/Vascular Cell Format

A vascular smooth muscle cell line and a vascular endothelial cell line are stably transfected with the estrogen responsive reporter pERE-Luc. The cells are grown and treated as described above. Agents which increase luciferase expression in both cell types are candidate vasoprotective agents.

Reporters Based on Growth-Promoting and Growth-Arrest Genes

Agents which cause vascular endothelial cells to proliferate or become activated without causing significant proliferation or activation of vascular smooth muscle cells or non-vascular cells or which cause inhibition of vascular smooth muscle cell proliferation are also candidate vasoprotective agents. Cell proliferation or activation can be measured directly by any conventional method, e.g., by monitoring $^3$H-thymidine uptake. In addition, cell proliferation and/or cell activation can be measured indirectly by measuring the expression of a reporter gene under the control of the upstream regulatory region of a growth-related gene. The growth related gene can be a gene whose expression is associated with growth, e.g., AP1 (fos/jun), c-myc, or c-myb or growth inhibition or arrest, e.g., p21, p27, p53, gas, gax, or Rb.

All or part of the upstream regulatory region of such a growth-related gene can be operably linked to the sequence encoding a detectable protein in order to provide a suitable reporter construct.

Assays Based on Growth Promoting Related Reporters or Growth Arrest Related Reporters A potential vasoprotective agent is one which increases the expression of a growth related gene in vascular endothelial cells, but which inhibits or does not significantly increase the expression of the same growth promoting related gene in vascular smooth muscle cells and/or non-vascular cells. An agent which increases the expression of a growth arrest related genes in vascular smooth muscle cells, but does not significantly increase the expression of the same growth arrest related gene in vascular endothelial cells is also a candidate vasoprotective agent.

Screening assays based on growth promoting related reporters or growth arrest related reporters can employ either of two preferred formats. Both formats involve at least three different cell types which harbor the same growth related reporter or growth arrest related reporter. The preferred assays use either a vascular cell line and a non-vascular cell line or a vascular cell line and a null cell line or a vascular endothelial cell line and a vascular smooth muscle cell line. However, other combinations may be used. Moreover, each format can employ more than one cell line of each type. The use of two or more different cell lines of the same type is desirable because, when the related cell lines exhibit the same response to a given candidate agent, one can be more certain that the effect of the agent will be similar for all cells of that type.

Agents Useful in Screening Assays

Agents for use in the screening assays of the invention can be obtained from any source. Libraries of synthetic and/or natural compounds are particularly useful. Numerous means are currently used for random and directed synthesis of saccharide, peptide, nucleic acid, and small molecule compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Libraries of natural compounds in the form of bacterial, fungal, plant and animal extracts are available from Pan Laboratories (Bothell, Wash.) and Myco-Search (N.C.). Phytoestrogens (Maleka et al., *Environ. Health Perspectives* 102:572, 1994; Knight et al., *Maturitas* 22:167, 1995) and the components of Premarin (Stern, *Maturitas* 4:33, 1982; Jayalilaka et al., *J. Organic Chrom.* 617:19, 1993) can also be screened using the methods of the invention.

Augmentation of Estrogen Receptor Expression

Under some circumstances, e.g., when the signal from the growth related reporter or the growth arrest related reporter is relatively low, it may be desirable to transfect the cells with an estrogen receptor expression construct in addition to the reporter construct. The estrogen receptor expression construct can express estrogen receptor α or estrogen receptor β. Under some circumstances it may be desirable to introduce both an estrogen receptor α expression construct and an estrogen receptor expression construct.

Estrogen Receptors

Estrogen receptor α is a transcription factor which belongs to the nuclear receptor superfamily. Like other members of the superfamily, estrogen receptor α, upon activation, e.g., by binding of its ligand, binds to DNA and alters gene expression. When estrogen receptor is complexed with its ligand, estrogen, it binds specific DNA sequences, as within the regulatory regions of a number of target genes. Whether the bound receptor has a positive or negative effect on the transcription of a given target gene, depends on both the cell type and the context of the regulatory region (Tzukerman et al., *Mol. Endocrin.* 8:21, 1994). The gene encoding estrogen receptor α has been cloned and shown to be functional in heterologous cells, including vascular cells, into which it has been introduced (Kumar et al., *EMBO J.* 5:2231, 1986; Green et al., *Science* 231:1150, 1986; Karas et al., *Circulation* 89:1943, 1994).

Estrogen receptor α is thought to include at least two important transcription activation domains. Binding of estrogen activates one of these domains, the transcription-activation factor-2 (TAF-2) domain. Activation of the other domain, the transcription-activation factor-1 (TAF-1) domain, is not dependent on estrogen binding, but may influence TAF-2 mediated transactivation and may be activated by other mechanisms such as phosphorylation via growth factor-mediated pathways.

Estrogen receptor β (Kuiper et al., *Proc. Nat'l Acad. Sci. USA* 93:5925, 1996; Genbank Accession Number U57439) is another estrogen receptor which may mediate the effects of estrogen on vascular cells. Rat estrogen receptor β, in the presence of estrogen, increases expression of a reporter gene under the control of a vitellogenin promoter estrogen response element.

Variant and Mutant Estrogen Receptors

In addition to wild-type estrogen receptors α and β, a number of variant estrogen receptors may be employed in the screening methods described below. Of particular interest are variant or mutant estrogen receptor which permit one to discriminate TAF-1 mediated effects and TAF-2 mediated effects. The variant estrogen receptors ESTROGEN RECEPTOR-S118A and ESTROGEN RECEPTOR-TAF2 are examples of estrogen receptors useful in some embodiments of the invention. The first of these mutants, ESTROGEN RECEPTOR-S118A, has a point mutation at amino acid 118. This mutation creates a molecule in which the TAF1 domain cannot be activated by phosphorylation of Ser 118. The second of these mutants, ESTROGEN RECEPTOR-TAF-2, has three mutations (at amino acids 538, 542, and 545) which together inactivate the TAF-2 domain so that the TAF-1 domain is the primary functional activation domain.

Production of Estrogen Receptors and Estrogen Receptor Variants

Any suitable expression construct can be used to express an estrogen receptor or an estrogen receptor variant. Estrogen receptor expression constructs can be used to express an estrogen receptor or an estrogen receptor variant in both cells which have an endogenous estrogen receptor and those which do not. For example, pCMV3-ESTROGEN RECEPTOR, plasmid which expresses estrogen receptor α expression construct was created by cloning the wild-type, human estrogen receptor α cDNA EcoRI fragment (Tora et al., *EMBO J.* 8:1981, 1989) into pCDNA3.1 (Invitrcgen). Constructs for expression of variant estrogen receptors, pCMV3-ESTROGEN RECEPTOR-S106A (coding for an alanine instead of a serine at amino acid position 106), pCMV3ER-S118A (coding for an alanine rather than a serine at position 118), pCMV3-ESTROGEN RECEPTOR-283 (in which a termination codon was introduced following amino acid 283), and pCMV3-ESTROGEN RECEPTOR-TAF2mut (in which amino acids 538, 542, and 545 where all changed to alanine), were constructed by site directed mutagenesis (Kunkel et al., *Proc. Nat'l Acad. Sci. USA* 82:488, 1985). A plasmid encoding a truncated version of the estrogen receptor containing only the A/B and C domains, pCMV3-ESTROGEN RECEPTOR-271, was constructed by excising from pCMV3-ESTROGEN RECEPTOR the coding sequence from the XcmI site at bp 815 to the end of the coding sequence.

A series of inducible estrogen receptor α expression constructs were created by cloning sequences encoding wild-type and variant estrogen receptor α into pUHD10-3 (*Mol. Cell. Biol.* 4:1669, 1994). This plasmid used in conjunction with either pUHD15-1neo (*Mol. Cell. Biol.,* 4:1669, 1994) or pUHD172-1neo (*Science* 268:1766, 1995) allow for tetracycline-responsive control of estrogen receptor expression. These additional estrogen receptor expression plasmids are referred to as: pTet-ESTROGEN RECEPTOR, pTet-ESTROGEN RECEPTOR-S106A, and pTet-ESTROGEN RECEPTOR-S118A. These inducible estrogen receptor expression constructs are useful for determining whether an observed effect on a cell is dependent on the presence of the estrogen receptor.

Expression constructs, including inducible constructs, for the expression of estrogen receptor β can be prepared as described above. DNA encoding estrogen receptor β can be obtained as described in Kuiper et al. (*Proc. Nat'l Acad. Sci. USA* 93:5925, 1996) or can be isolated by PCR cloning using primers based on sequences disclosed in Kuiper et al. (*Proc. Nat'l Acad. Sci. USA* 93:5925, 1996).

Detectable Proteins

The reporter constructs can employ any suitable detectable protein, e.g., luciferase, green flourscent protein, or chloramphenicol acetyl transferase (CAT).

Vascular Endothelial Cell and Vascular Smooth Muscle Cell Co-Culturing Methods

Both the assays based on estrogen responsive reporter and the assays based in growth related or growth arrest related reporters can be performed using a co-culturing format. In a co-culturing assay any vascular endothelial cell line is grown in co-culture with a vascular smooth muscle cell line and any vascular smooth muscle cell line is grown in co-culture with a vascular endothelial cell line. Co-culturing can be accomplished by actually growing a mixed cell culture or by using a Transwell® cell culture insert (Costar Corp.). The second vascular cell line does not contain a reporter construct; it is present to provide the first vascular cell line (i.e., the reporter harboring cell line) with an environment which more closely resembles that found in vivo.

In vivo Model for Screening Vasoprotective Agents

Vasoprotective agents identified using the screening methods described herein can be tested in various animal models of vascular injury. For example, agents identified using the method described herein can be tested in the mouse cartoid artery injury model described by Linder et al. (*Circ. Res.* 73:792, 1993). Agents may also be tested using the porcine femoral injury model. (Nabel et al., *Science* 249:1285, 1990; Nabel et al., *Nature* 362:844, 1993;* and Ohno et al., *Science* 265:781, 1994).

Induction of Estrogen Responsive Genes by Estrogen

To study the role of estrogen on expression of the VEGF gene in vascular smooth muscle cells, human saphenous vein smooth muscle cells (HSVSMC) and HeLa cells were transiently transfected with a VEGF-luciferase reporter construct. In this reporter construct, expression of luciferase is under the control of a 1.2 kB fragment of the murine VEGF gene regulatory region. The cells were also transfected with an estrogen receptor α expression construct. All of the results described below have been normalized for transfection efficiency..

The luciferase expression of VEGF-luciferase transfected HSVSMC was increased 1.7±0.2 fold (n=12, p<0.02) when the cells were grown in the presence of 1 μM estrogen. To confirm that this activation of luciferase expression was estrogen receptor α dependent, HeLa cells, which do not posses endogenous estrogen receptor α, were also studied. Growth of VEGF-luciferase reporter transfected HeLa cells in estrogen containing media had no effect on luciferase expression. However, if the cells were co-transfected with an estrogen receptor α expression plasmid, growth in estrogen containing media increased luciferase expression 4.2±0.8-fold (n=21, p<0.03).

Estrogen Activates Vascular Endothelial Growth Factor Expression in Human Vascular Cells but not in Non-vascular Cells The following experiments demonstrate that estrogen activates VEGF expression in vascular cells (WB572 cells), but not in non-vascular cells such as rat pituitary cells (GH3B6). In these experiments WB572 cells and GHB6 cells were transiently transfected with the pmVEGF-Luc reporter construct either with or without an expression plasmid for estrogen receptor α. The cells were cultured for 48 hours in the absence or presence of estrogen ($10^{-6}$M) and luciferase expression was measured. Estrogen induced a 1.8-fold increase in luciferase activity in WB572 cells, but had no effect in GH3B6 cells. The ability of the GH3B6 cells to respond to estrogen was confirmed by transfection of the pERE-Luc reporter which was activated 8-fold under the same conditions. Interestingly, similar experiments performed with rat VSMC (A7r5 cells) demonstrated that estrogen did not activate VEGF expression in these cells either. Thus, the effects of estrogen on gene expression can depend both on the type of cells studied as well as on the species from which the cell is derived.

Mitogen-mediated (Ligand Independent) Activation of the Estrogen Receptor in Vascular Cells is Cell-type Dependent The following experiments demonstrate that the estrogen receptor is activated in cells by mitogenic stimulation with epidermal growth factor (EGF), but that this activation is dependent on the type of cell studied. In these experiments three varieties of vascular cells (PVEC, HSVSMC, and human aortic VSMC) and the non-vascular cell-type HeLa cells, were transiently transfected with the reporter plasmid ERE-Luc and an expression plasmid for the estrogen receptor. The cells were then cultured for 48 hours in serum-free medium in the absence or presence of EGF (100 ng/ml). The degree to which the estrogen receptor is able to activate the ERE is then determined by measuring luciferase activity in cell lysates. In all three types of vascular cells, EGF induced approximately a 3-fold increase in luciferase activity. In HeLa cells, EGF had no effect. The cell-type specificity of the EGF effect was demonstrated in these same experiments by showing (a) either estrogen or FBS induced similar increases in receptor activation in all cell types studied, and (b) PDGF did not activate the estrogen receptor in any cell type studied.

Estrogen Inhibition of Medial Vascular Smooth Muscle Cell Proliferation Occurs via a Pathway Which is not Dependent on Estrogen Receptor α

The experiments described below demonstrate that estrogen inhibition of medial vascular smooth muscle cell proliferation is mediated, principally, by a estrogen receptor α-independent pathway.

The effects of estrogen on the vascular injury response were studied in estrogen receptor α knockout (Lubahm et al., *Proc. NAt'l. Acad. Sci. USA* 90:11162, 1993) mice and their littermate controls using a cartoid injury model. Vascular medial are increases and smooth muscle cell proliferation were quantitated 14 days following cartoid injury in ovariectomized female mice treated with vehicle or physiologic levels of 17-β estradiol. Suprisingly, 17-β estradiol markedly inhibited all measures of vascular injury both in wild-type and estrogen receptor α knockout mice to the same degree. These data suggest that estrogen inhibits vascular injury by a novel mechanism that is independent of estrogen receptor α.

Use

The present invention also encompasses pharmaceutical compositions which include a vasoprotective agent identified using the above-described methods. These compositions include a pharmaceutically effective amount of the vasoprotective agent in a pharmaceutically acceptable carrier or diluent. Acceptable carriers or diluents for therapeutic use are well known in the pharmaceutical art, and are described, for example, in *Remington's Pharmaceutical Sciences,* Mack Publishing Co. (Gennaro ed., 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compositions of the present invention may be formulated and used as tablets, capsules or elixirs for oral administration, suppositories for rectal administration, sterile solutions, suspensions for injectable administration, and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The pharmaceutically effective amount of the composition required as a dose will depend on the route of administration, the type of animal being treated, and the physical characteristics of the specific animal under consideration. The dose can be tailored to achieve optimal efficacy but will depend on such factors as weight, diet, concurrent medication and other factors which those skilled in the medical arts will recognize. Typically, human clinical applications of products are commenced at lower dosage levels, with dosage level being increased until the desired effect is achieved. The determination of effective dosage levels, that is the dosage levels necessary to achieve the desired result, will be within the ambit of one skilled in the art based on generally accepted protocols for clinical studies.

In practicing the methods of the invention, the vasoprotective agents can be used alone or in combination with one another, or in combination with other therapeutic or diagnostic agents. A vasoprotective agent can be administered parenterally, intravenously, subcutaneously, intramuscularly, colonically, rectally, nasally or intraperitoneally, employing a variety of dosage forms.

What is claimed is:

1. A method for evaluating whether an agent is a cardiovascular therapeutic agent, comprising:
    (a) culturing vascular endothelial cells containing an estrogen responsive gene in the presence and absence of a predetermined amount of said agent;
    (b) culturing non-vascular cells containing said estrogen responsive gene in the presence and absence of said predetermined amount of said agent; and
    (c) measuring the expression of said estrogen responsive gene in said vascular endothelial cells in the presence and absence of said predetermined amount of said agent and measuring the expression of said estrogen responsive gene in said non-vascular cells in the presence and absence of said predetermined amount of said agent;
    whereby said agent is identified as a cardiovascular therapeutic agent when the ratio of the expression of said estrogen responsive gene in said vascular endothelial cells in the presence of said predetermined amount of said agent to the expression of said estrogen responsive gene in vascular endothelial cells in the absence of said predetermined amount of said agent is greater than the ratio of the expression of said estrogen responsive gene in said non-vascular cells in the presence of said predetermined amount of said agent to the expression of said estrogen responsive gene in non-vascular cells in the absence of said predetermined amount of said agent.

2. A method for evaluating whether an agent is a cardiovascular therapeutic agent, comprising:
    (a) culturing vascular smooth muscle cells containing an estrogen responsive gene in the presence and absence of a predetermined amount of said agent;
    (b) culturing non-vascular cells containing said estrogen responsive gene in the presence and absence of said predetermined amount of said agent; and
    (c) measuring the expression of said estrogen responsive gene in said vascular smooth muscle cells in the presence and absence of said predetermined amount of said agent and measuring the expression of said estrogen responsive gene in said non-vascular cells in the presence and absence of said predetermined amount of said agent;
    whereby said agent is identified as a cardiovascular therapeutic agent when the ratio of the expression of said estrogen responsive gene in said vascular smooth muscle cells in the presence of said predetermined amount of said agent to the expression of said estrogen responsive gene in vascular smooth muscle cells in the absence of said predetermined amount of said agent is less than the ratio of the expression of said estrogen responsive gene in said non-vascular cells in the presence of said predetermined amount of said agent to the expression of said estrogen responsive gene in non-vascular cells in the absence of said predetermined amount of said agent.

3. A method for evaluating whether an agent is a cardiovascular therapeutic agent, said method comprising:
    (a) culturing vascular endothelial cells containing an estrogen responsive gene in the presence and absence of a predetermined amount of said agent;
    (b) culturing non-estrogen receptor expressing cells containing said estrogen responsive gene in the presence and absence of said predetermined amount of said agent; and
    (c) measuring the expression of said estrogen responsive gene in said vascular endothelial cells in the presence and absence of said predetermined amount of said agent and measuring the expression of said estrogen responsive gene in said non-estrogen receptor expressing cells in the presence and absence of said predetermined amount of said agent;
    whereby said agent is identified as a cardiovascular therapeutic agent when the ratio of the expression of said estrogen responsive gene in said vascular endothelial cells in the presence of said predetermined amount of said agent to the expression of said estrogen responsive gene in vascular endothelial cells in the absence of said predetermined amount of said agent is greater than the ratio of the expression of said estrogen responsive gene in non-estrogen receptor expressing cells in the presence of said predetermined amount of said agent to the expression of said estrogen responsive gene in non-estrogen receptor expressing cells in the absence of said predetermined amount of said agent.

4. A method for evaluating whether an agent is a cardiovascular therapeutic agent, said method comprising:
    (a) culturing vascular smooth muscle cells containing an estrogen responsive gene in the presence and absence of a predetermined amount of said agent;

(b) culturing non-estrogen receptor expressing cells containing said estrogen responsive gene in the presence and absence of said predetermined amount of said agent; and (c) measuring the expression of said estrogen responsive gene in said vascular smooth muscle cells in the presence and absence of said predetermined amount of said agent and measuring the expression of said estrogen responsive gene in said non-estrogen receptor expressing cells in the presence and absence of said predetermined amount of said agent;

whereby said agent is identified as a cardiovascular therapeutic agent when the ratio of the expression of said estrogen responsive gene in said vascular smooth muscle cells in the presence of said predetermined amount of said agent to the expression of said estrogen responsive gene in vascular smooth muscle cells in the absence of said predetermined amount of said agent is less than the ratio of the expression of said estrogen responsive gene in said non-estrogen expressing cells in the presence of said predetermined amount of said agent to the expression of said estrogen responsive gene in non-estrogen expressing cells in the absence of said predetermined amount of said agent.

5. A method for evaluating whether an agent is a cardiovascular therapeutic agent, said method comprising:

(a) culturing vascular endothelial cells containing an estrogen responsive gene in the presence and absence of a predetermined amount of said agent;

(b) culturing vascular smooth muscle cells containing said estrogen responsive gene in the presence and absence of said predetermined amount of said agent; and (c) measuring the expression of said estrogen responsive gene in said vascular endothelial cell in the presence and absence of said predetermined amount of said agent and measuring the expression of said estrogen responsive gene in said vascular smooth muscle cells in the presence and absence of said predetermined amount of said agent;

whereby said agent is identified as a cardiovascular therapeutic agent when the ratio of the expression of said estrogen responsive gene in said vascular endothelial cells in the presence of said predetermined amount of said agent to the expression of said estrogen responsive gene in vascular endothelial cells in the absence of said predetermined amount of said agent is greater than the ratio of the expression of said estrogen responsive gene in said vascular smooth muscle cells in the presence of said predetermined amount of said agent to the expression of said estrogen responsive gene in vascular smooth muscle cells in the absence of said predetermined amount of said agent.

6. The method of any of claims 1, 2, 3, 4, or 5, wherein said estrogen responsive gene is a vitellogenin, progesterone, prolactin receptor, nucleophosmin, prostaglandin cyclooxygenase, prostaglandin synthase, constitutive or calcium-dependent nitric oxide synthase, collagen, elastin, c-fos, progesterone receptor, vascular endothelial growth factor, epidermal growth factor receptor, interleukin-6, neu, egr-1, estrogen receptor, heat shock protein 27, vascular adhesion molecule, vascular smooth muscle cell calcium channel, ryanodine receptor, FLT4 receptor tyrosine kinase, fibroblast growth factor receptor, inducible nitric oxide synthase, insulin-like growth factor, insulin-like growth factor receptor, transforming growth factor α, c-myc, c-fos, c-jun, antithrombin III (protein S), apolipoprotein A, B, D, or E, INT-2 protooncogene, apolipoprotein II, or calcium-independent nitric oxide synthase gene.

7. The method of any of claims 1, 2, 3, 4, or 5, wherein said estrogen responsive gene is an endogenous, genomic gene.

8. The method of any of claims 1, 2, 3, 4, or 5, wherein said estrogen responsive gene is a non-endogenous gene.

9. The method of claims 2, 4, and 5, wherein said vascular smooth muscle cells are WB572 cells.

10. The method of any of claims 1, 2, 3, 4, or 5, be wherein said cells are co-transfected with an estrogen receptor expression construct.

11. The method of claim 10, wherein said estrogen receptor expression construct expresses estrogen receptor α.

12. The method of claim 10, wherein said estrogen receptor expression construct expresses estrogen receptor β.

* * * * *